(12) United States Patent
Tilghman

(10) Patent No.: US 8,664,466 B2
(45) Date of Patent: Mar. 4, 2014

(54) HOOF BANDAGES

(76) Inventor: Bryan K. Tilghman, Maryville, TN (US)

( * ) Notice: Subject to any disclaimer, the term of this patent is extended or adjusted under 35 U.S.C. 154(b) by 1183 days.

(21) Appl. No.: 12/140,516

(22) Filed: Jun. 17, 2008

(65) Prior Publication Data

US 2009/0149793 A1    Jun. 11, 2009

Related U.S. Application Data

(63) Continuation-in-part of application No. 11/156,383, filed on Jun. 20, 2005, now abandoned, and a continuation-in-part of application No. 10/921,778, filed on Aug. 19, 2004, now abandoned.

(51) Int. Cl.
*A61F 13/00* (2006.01)
*A01K 13/00* (2006.01)
*A01L 15/00* (2006.01)

(52) U.S. Cl.
USPC .................................. 602/58; 119/850; 168/2

(58) Field of Classification Search
USPC ........... 602/23, 28, 29, 30, 41–45, 60–65, 75, 602/79; 128/856, 846, 878–882, 892–894; D30/144, 146–150, 199; 119/850, 851; 168/26–28; 54/82, 1
See application file for complete search history.

(56) References Cited

U.S. PATENT DOCUMENTS

| | | | |
|---|---|---|---|
| 3,334,625 A | | 8/1967 | Baron |
| 3,508,544 A | * | 4/1970 | Moore et al. .................. 128/892 |
| 4,921,155 A | | 5/1990 | Ito et al. |
| 5,224,549 A | | 7/1993 | Lightner |
| 5,389,061 A | * | 2/1995 | Nor ................................ 600/15 |
| 5,592,953 A | | 1/1997 | Delao |
| 6,122,901 A | * | 9/2000 | Schultz et al. .................... 54/82 |
| 6,546,704 B1 | | 4/2003 | Fisher |

OTHER PUBLICATIONS

Huber Textiles, Inc. Style: 600 Denier Polyester Date Sheet (date unknown) Fallston, NC USA.
Tyco International, Ltd Co 105 C Polyken Industrial Tapes (date unknown) Norwood, MA USA.

* cited by examiner

*Primary Examiner* — Patricia Bianco
*Assistant Examiner* — Tarla Patel
(74) *Attorney, Agent, or Firm* — Luedeka Neely Group, PC

(57) ABSTRACT

A bandage for a hoof, including a sheet material having a central body portion and a plurality of palmate lobes radiating outwardly from a central body portion. Straps extend from opposed sides of a lobe adjacent the back side of the hoof and are secured to an exterior portion of the bandage adjacent the toe of the hoof when the bandage is installed on the hoof.

3 Claims, 11 Drawing Sheets

HOOF BANDAGES

CROSS-REFERENCE TO RELATED APPLICATION

This is a continuation-in-part of co-pending U.S. application Ser. No. 11/156,383 filed Jun. 20, 2005 and entitled "Hoof Bandages," which is a continuation-in-part of U.S. application Ser. No. 10/921,778 filed Aug. 19, 2004 and entitled "Abrasion Resistant Tape And Uses Therefor" (abandoned).

FIELD OF THE INVENTION

This invention relates to bandaging and, in particular, to bandaging configured for hooves.

BACKGROUND AND SUMMARY OF THE INVENTION

Typically, hooves of animals, such as horses, are bandaged by wrapping tape, such as duct tape, around portions of the hoof including edges of the hoof to secure a pad or other bandage material in place. However, such bandages have numerous shortcomings and improvement is desired.

Described herein, in one aspect, is a hoof bandage including a sheet material having a central body portion and a plurality of palmate lobes radiating outwardly from a central body portion. One of the lobes is located to substantially surround a back side of the hoof and includes straps that extend from opposed sides of such lobe adjacent the back side of the hoof toward a toe of the hoof. The straps are secured to an exterior portion of the bandage adjacent the toe of the hoof when the bandage is installed on the hoof.

BRIEF DESCRIPTION OF THE DRAWINGS

Further features of preferred embodiments of the invention will become apparent by reference to the detailed description of preferred embodiments when considered in conjunction with the figures, wherein like reference numbers, indicate like elements through the several views, and wherein.

DETAILED DESCRIPTION

FIGS. 1-9

Figure 1:
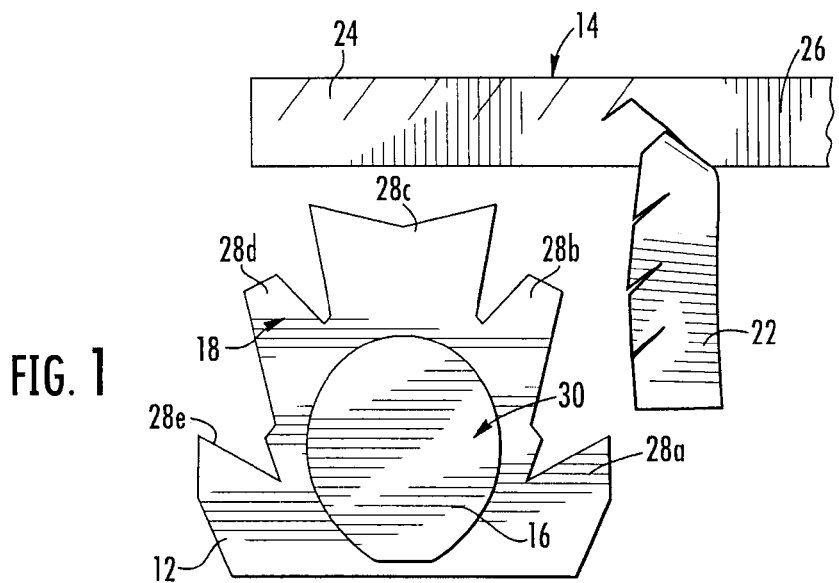
FIG. 1 shows a hoof bandaging system in accordance with a preferred embodiment of the invention.

The invention relates to a novel tape combination that provides a tape structure having improved abrasion resistance and that is suitable for a variety of uses under which conventional tapes quickly abrade and need frequent replacement.

The invention also relates to configurations that preferably utilize the tape and are particularly suitable for use in bandaging applications for livestock hooves and the like. It has been observed that the tape is exceptionally durable as compared to conventional tapes commonly used for bandaging hooves, such as duct tape.

The tape is preferably made by use of a conventional adhesive substrate, preferably a double coated tape material, to which is mated a strip of a polyester fiber sheet material. A preferred adhesive substrate is a double coated tape material available under the tradename POLYKEN 105C from Tyco Adhesives of Norwood, Mass. This material has a cloth backing or carrier material that is coated on both sides with a rubber-based adhesive. A silicone-coated release liner is applied to one of the adhesive surfaces. Another preferred adhesive substrate is a polyester-supported laminating adhesive available under part number B600-STD from John Deal Coatings, Inc. (a/k/a JDC Inc.) of Mt. Juliet, Tenn.

In accordance with the invention, a strip of a polyester fiber sheet material, preferably having a width corresponding to the width of the double coated tape material, is applied to the adhesive surface of the double coated tape material opposite the adhesive surface to which the release liner is applied. The polyester fiber sheet is preferably a sheet material made of polyester fiber and having a denier of from about 200 to about 2000, most preferably about 600 denier.

A particularly preferred polyester fiber sheet material is a material available under the tradename 600. Poly from Huber Textiles of Fallston, N.C. The 600 Poly material is a 600 denier polyester fiber sheet material having a weight of about 420 grams per linear yard, with a warp count per inch (CPI) of about 45 and a fill CPI of about 30. A ¾ oz polyurethane coating is preferably applied to the material to improve water repellency properties.

Another preferred polyester fiber sheet material is a material known as 1050 Ballistic Nylon, having the following characteristics:

warp: 1050 denier, 44 ends per inch
  fill: 1050 denier, 40 picks per inch
  weave: 2×2 basket
  fiber; 100% nylon
  coating: 1¼ to 1½ oz. urethane
  finish: water repellency It has been observed that tape made in according with the foregoing description has improved abrasion resistance as compared to conventional tape materials, such as duct tape, and may be suitable for a variety of uses of the type duct tape and other conventional tapes are normally used for. The tape of the invention is believed to be particularly suitable for applications wherein the tape will be subjected to abrasive forces, such as a patch for luggage, upholstery and the like, as well as a wide variety of applications.

In this regard, it has been observed that the tape is particularly suitable for use in bandaging hooves. It has been observed that a bandage material, such as gauze or the like, applied to a horse hoof using duct tape typically lasts no more than about a day, with the tape abrading and the bandage falling off due to the horse walking. To the contrary, it has been observed that a bandage applied using tape according to the invention lasts considerably longer than a day, often up to a week. As will be appreciated, this advantageously avoids the time and effort needed to maintain the bandage.

Figure 2:
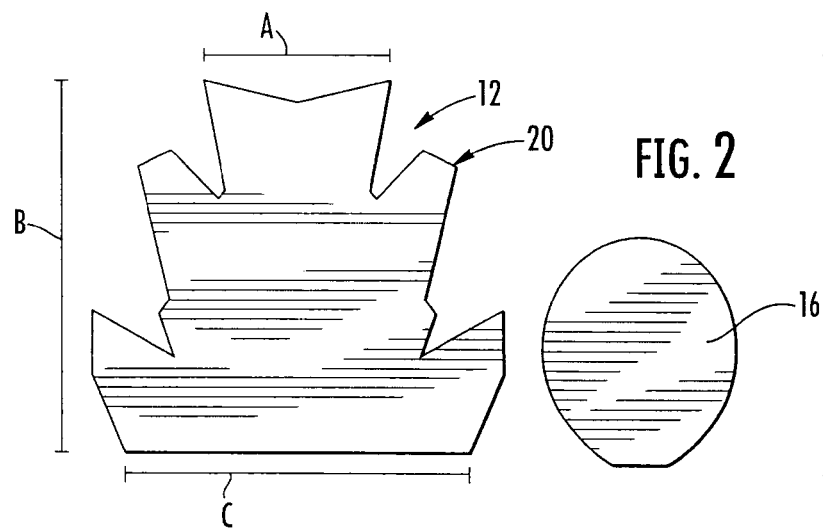
FIG. 2 shows the exterior of a main body portion and a pad member of the bandaging system of FIG. 1.

In another aspect, and with reference to FIGS. 1-2, the invention relates to a horse bandaging system 10 having a hoof bandage 12 and a securement strip 14. A padding material, such as a cotton or foam pad 16 is also preferably included.

The bandage 12 and the securement strip 14 are each preferably made of the tape material of the invention described above. For example, the bandage 12 is provided by a double coated tape material 18 to which is mated to a correspondingly configured polyester fiber sheet material 20, with a release liner preferably applied to the exposed adhesive surface of the tape material 18. Likewise, the securement strip 14 is provided by a double coated tape material 22 to which is mated to a correspondingly configured polyester fiber sheet material 24, with a release liner 26 preferably applied to the exposed adhesive surface of the tape material 22. For use in connection with bandaging hooves, the polyester fiber sheet material 20 preferably has a denier of from about 200 to about 1000, most preferably from about 400 to about 600 denier.

The bandage 12 is configured to be placed under the hoof of a horse (or other livestock) and to have a plurality of independently foldable portions so as to enable the bandage to be applied to the hoof in a manner that enables the installed bandage 12 to lie flat against the profiles of the hoof. For example, the bandage 12 is preferably configured from a sheet of the tape material, as by cutting, to have a shape generally resembling the shape of a maple leaf and including five palmate lobes 28a, 28b, 28c, 28d, and 28e radiating outwardly from a central body portion 30 of the bandage 12 onto which the pad 16 is preferably adhered. It will be understood that the bandage 12 may be provided in a variety of dimensions, with the preferred dimensions being selected to correspond to the size of the hoof being bandaged. However, for the purpose of example only, and with reference to FIG. 2, the bandage 12 may preferably have the following dimensions, with the upper range being particularly preferred:

| Dimension | Length (inches) |
|---|---|
| A | 4.5 to 6 |
| B | 8.5 to 11 |
| C | 8.0 to 9.5 |

Figure 3:
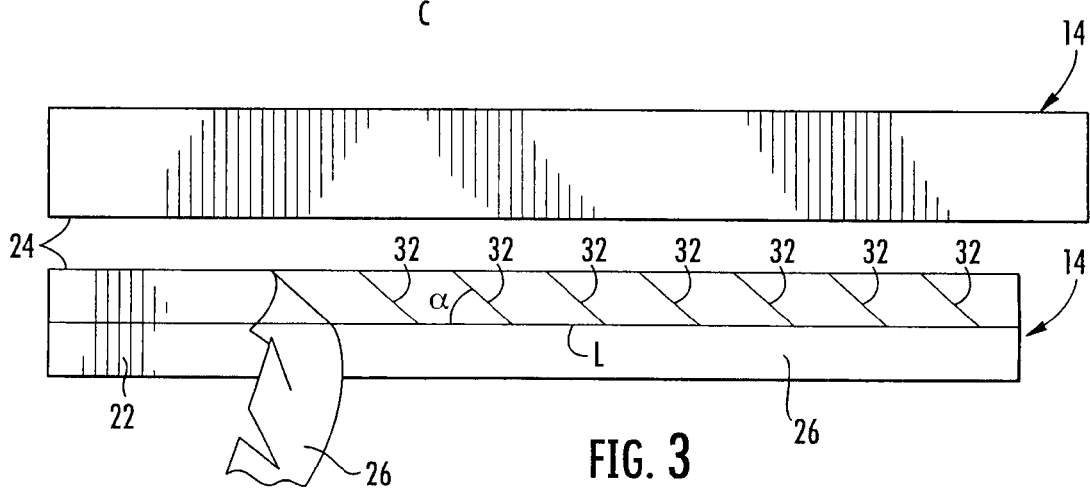
FIG. 3 shows the top and bottom of a tape member of the bandaging system of FIG. 1.

With reference to FIG. 3, the securement strip 14 is preferably configured to have a length of about 15 to 25 inches, most preferably about 20 inches and a width of about 2 inches for use with the bandage 14 configured as described above. However, it will be understood that the strip 14 may be provided in a variety of lengths and widths. In addition, the securement strip 14 is incrementally cut to define a plurality of slits 32 along the length thereof. For the above dimensioned strip 14, and for the purpose of example only, the slits 32 are preferably uniformly spaced apart by a distance of about 1½ inches and extend in a direction toward a lateral line L of the strip 14. The slits 32 preferably extend about half of the width of the strip 14 and are disposed at an angle of about 45 degrees. However, it will be understood that the slits 32 may be provided in other orientations and dimensions.

It has been discovered that the described configuration of the strip 14 facilitates installation of the strip 14 about the circumference of a hoof. The securement strip 14 is preferably utilized in conjunction with the bandage 12, but is also suitable for use in securing gauze and other conventional bandaging materials, and for providing structural support to help protect the integrity of the hoof wall.

Figure 4:
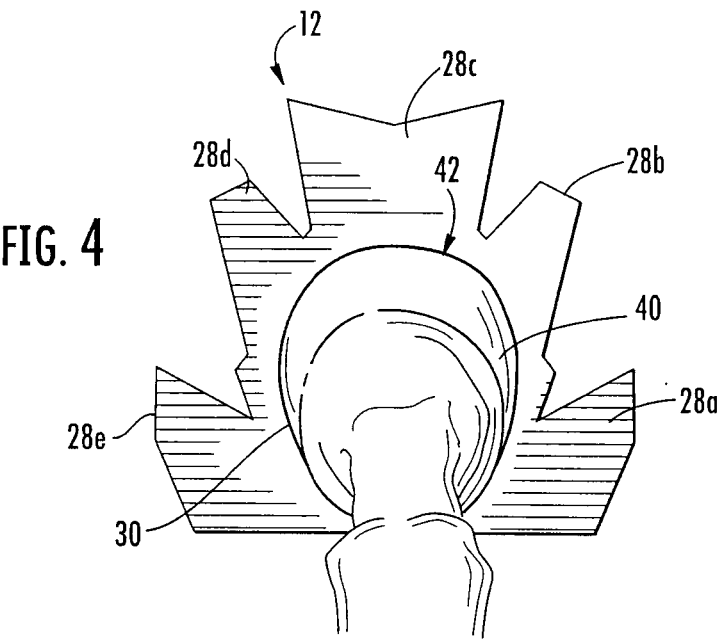
FIGS. 4-9 show preferred steps in the application of the bandaging system of FIG. 1 to a hoof.

Turning now to FIGS. 4-9, there are shown preferred steps in the application of the bandaging system 10 to a hoof 40. As seen in FIG. 4, the sole of the hoof 40 is positioned on the central body portion 30 of the tape material 18 and oriented such that the toe 42 of the hoof 40 is located below the lobe 28c of the bandage 12. The pad 16 is preferably placed under the hoof 40. It will be understood that the pad 16 is suitable for providing comfort attributes and may also serve as a site for receiving medicament and the like.

Figure 5:
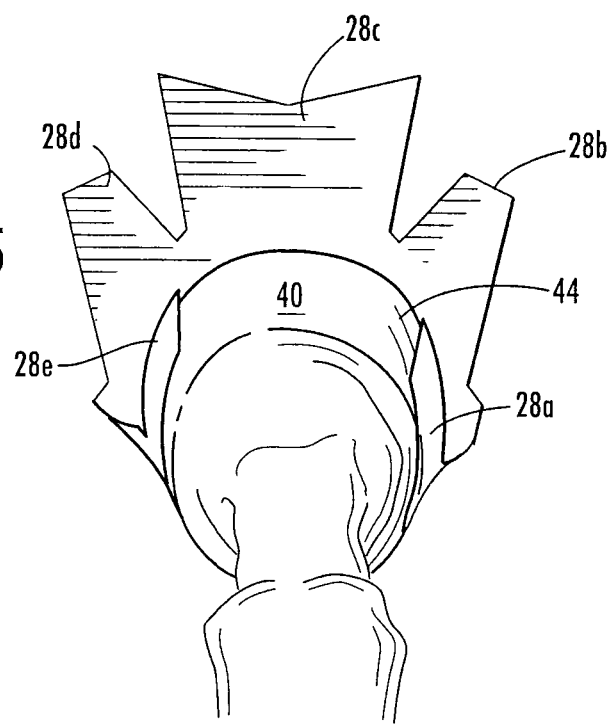
Figure 6:
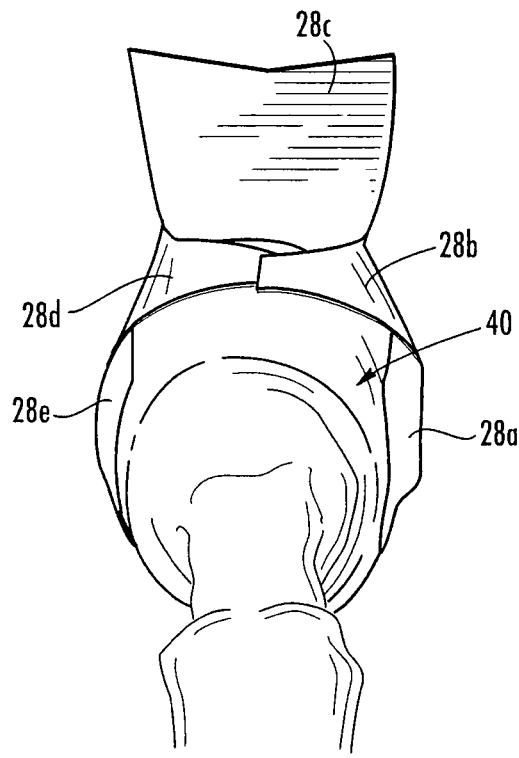
Figure 7:
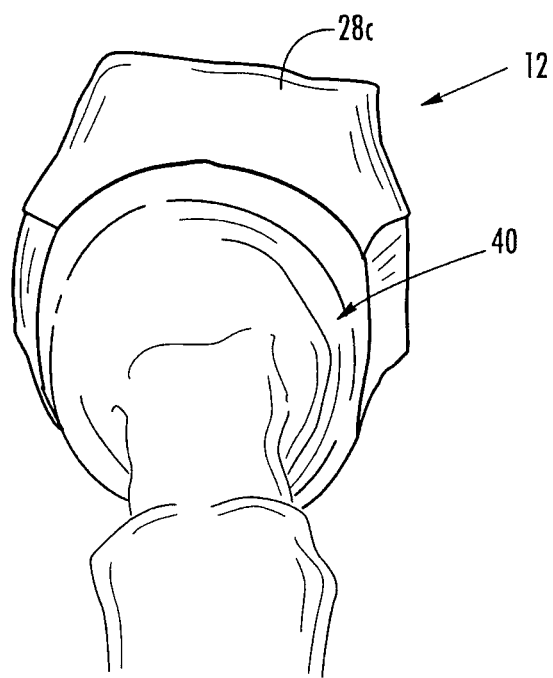

Next, as seen in FIG. 5, the lobes 28a and 28e are folded about proximate portions of wall 44 of the hoof 40 and secured to the wall 44 of the hoof by the adhesive of the tape material 18. Proceeding to FIG. 6, the lobes 28b and 28d are folded and secured to proximate portions of the wall 44 of the hoof 40 and overlie a portion of the lobes 28a and 28e, respectively. Next, to complete the installation of the bandage 12 and as shown in FIG. 7, the lobe 28c is folded and secured to the wall 44 and substantially overlies the lobes 28b and 28d.

Figure 8:
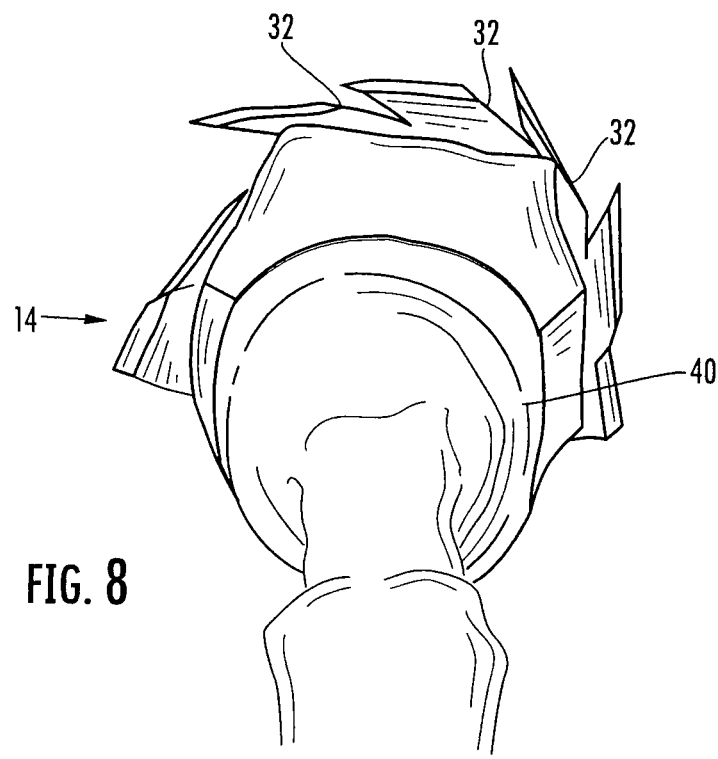
Figure 9:
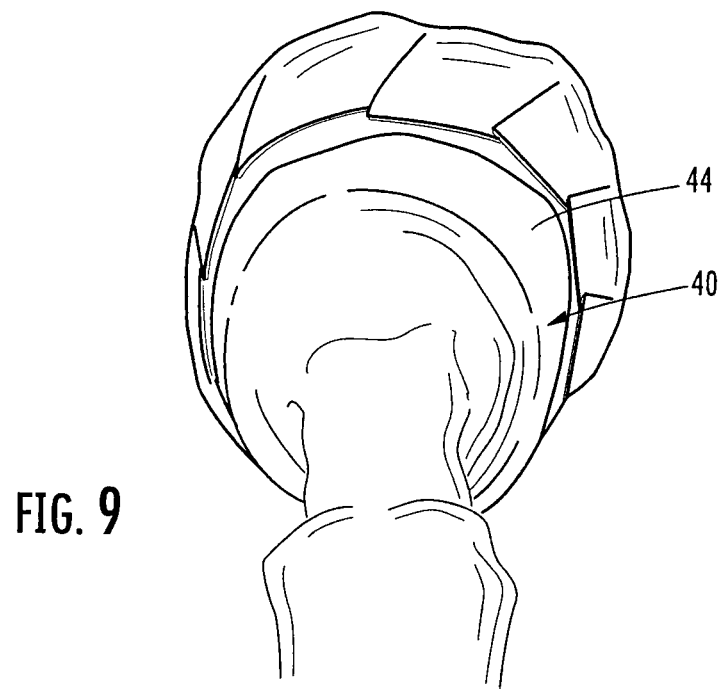

With reference to FIG. 8, the strip 14 is positioned to extend from the lobe 28a to the lobe 28e and around the toe 42 of the hoof, with the portion thereof not having the slits 32 being adhesively secured over the bandage 12 adjacent the sole of the hoof 40. Following this, as shown in FIG. 9, the portions of the strip 14 corresponding to the slits 32 are adhesively secured adjacent the wall 44 of the hoof 40 to complete the preferred installation of the bandaging system 10.

The bandaging system 10 advantageously provides a light and durable system that can be used to bandage hooves and is also easily portable so as to render it suitable for use as an emergency device in the field. For example, horses often drop a shoe when in the field or on the trail. The bandaging system 10 (as well as simply the tape of the invention) may be applied to protect the hoof to enable the horse to be ridden home. The bandage and/or tape may also be utilized to retain a loose shoe or protect the unshod hoof while awaiting the services of the farrier.

FIGS. 10-12

Figure 10:
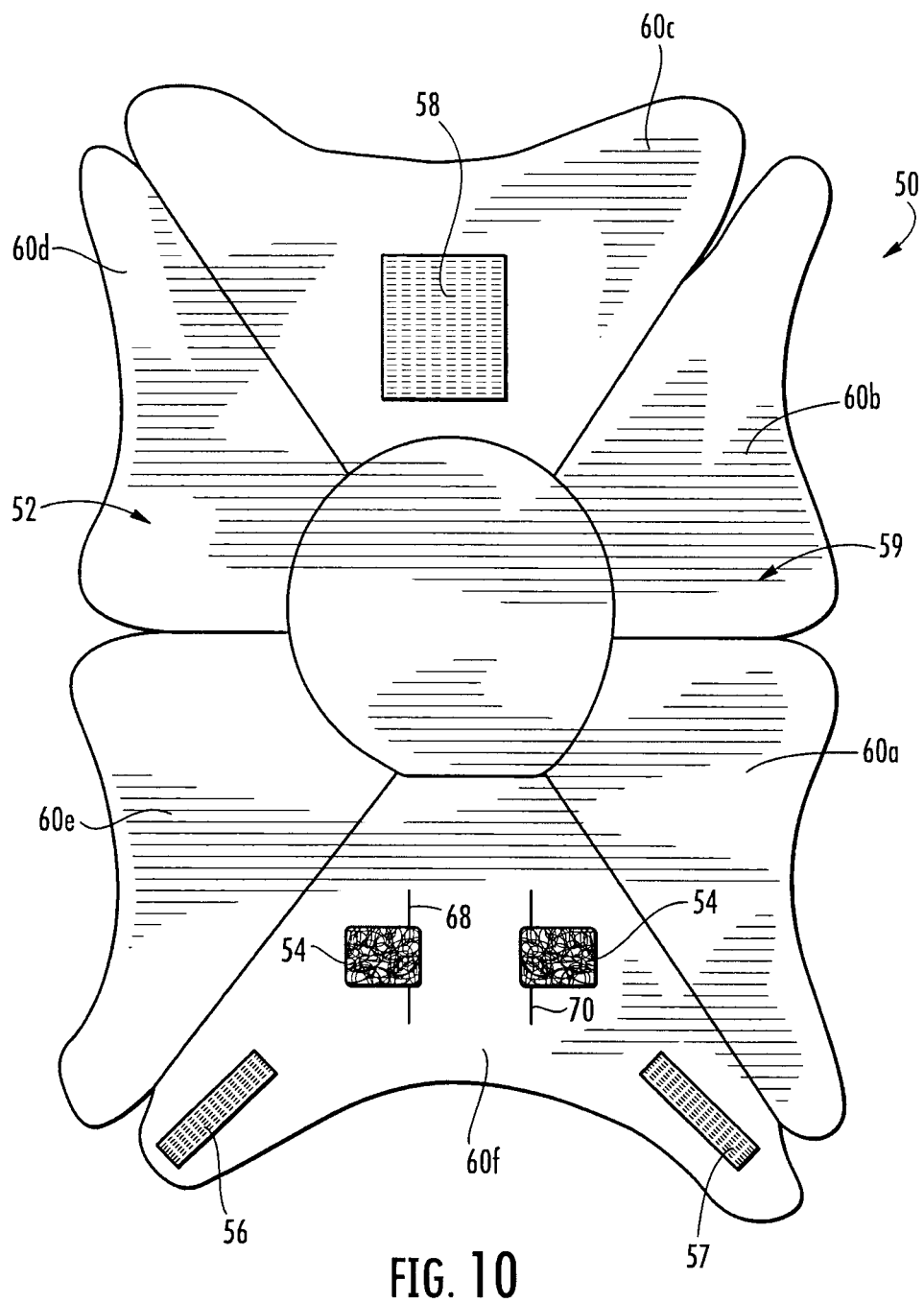
FIG. 10 shows the exterior of an alternate embodiment of a bandage as laid flat.
Figure 11:
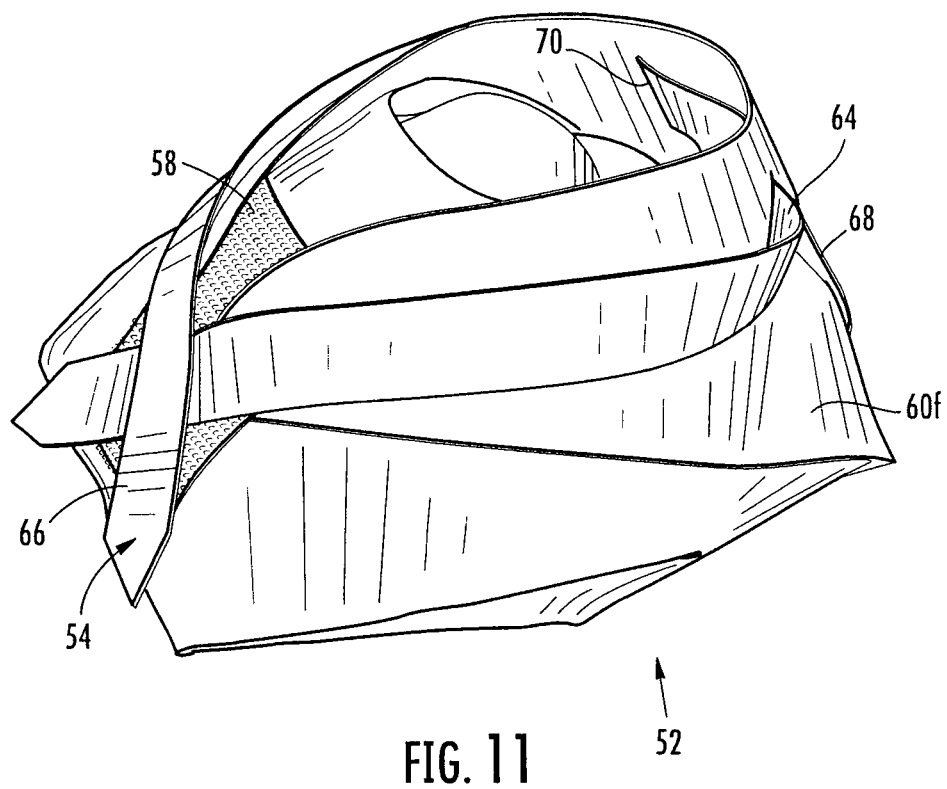
FIG. 11 shows the bandage of FIG. 10 folded as if applied to a hoof.
Figure 12:
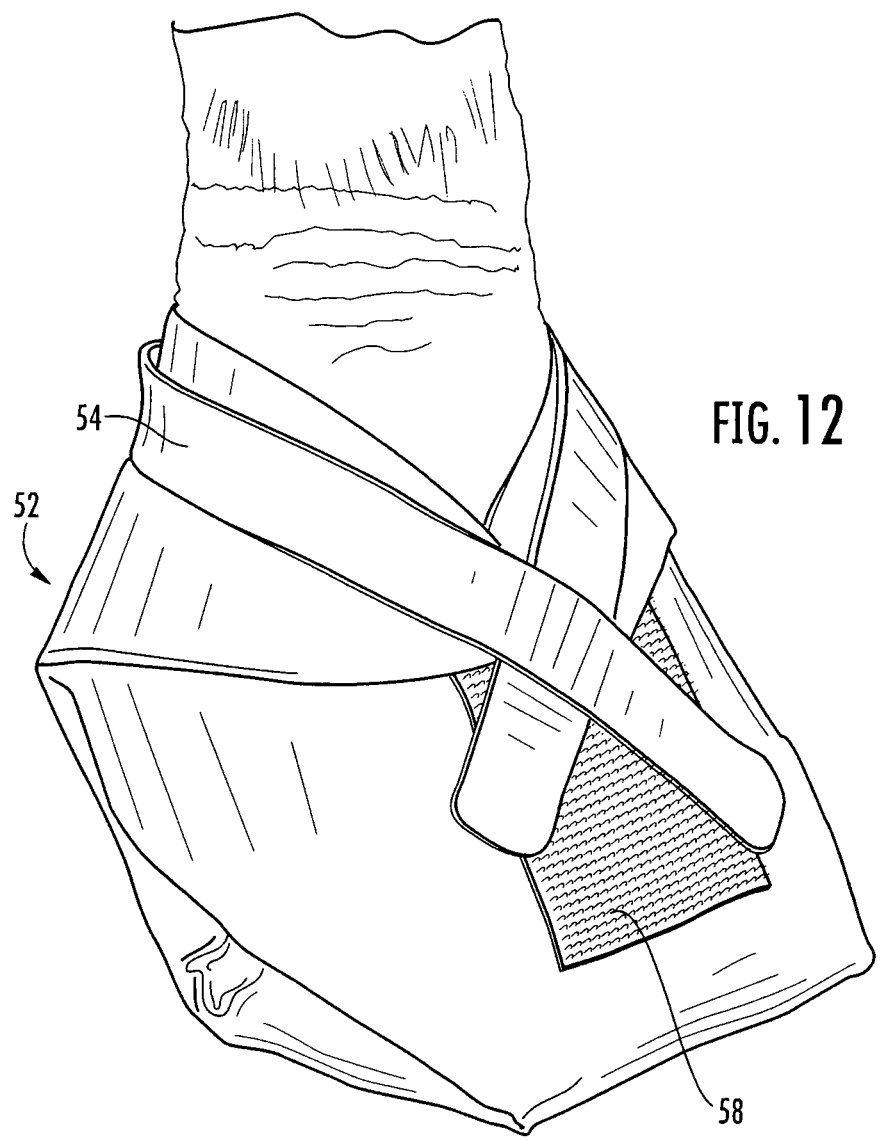
FIG. 12 shows the bandage of FIG. 10 applied to a hoof of a horse.

With reference now to FIGS. 10-12, there is shown an alternate embodiment of a bandaging system 50. The system 50 includes a bandage 52 having securement devices, preferably, a strap 54 and cooperating strap engaging members, such as cooperating strap engagement members 56, 57, and 58, integrated therewith.

The bandage 52 is preferably made of the tape material described above. For example, the bandage 52 may preferably be provided by a double coated tape material to which is mated to a correspondingly configured polyester fiber sheet material, with a release liner preferably applied to the exposed adhesive surface of the tape material. FIG. 1 shows an exterior surface 59 of the bandage 52, which is made of the polyester fiber sheet material, it being understood that the opposite surface of the bandage 52 is provided by the tape material and is the surface that is positioned adjacent the hoof. The bandage 52 is configured to be placed under the hoof of a horse (or other livestock) and to have a plurality of independently foldable portions so as to enable the bandage to be applied to the hoof in a manner that enables the installed bandage 52 to lie flat against the profiles of the hoof. For example, the bandage 52 is preferably configured from a sheet of the tape material, as by cutting, to have a shape including palmate lobes 60a, 60b, 60c, 60d, 60e, and 60f radiating outwardly from a central body portion 62 of the bandage 52. If desired, a pad, such as the pad 16 described previously, may preferably be adhered to the body portion.

It will be understood that the bandage 52 may be provided in a variety of dimensions, with the preferred dimensions being selected to correspond to the size of the hoof being bandaged. It will further be understood that the bandage may include fewer or more of the lobes. For example, individual lobes may be bifurcated and made into two lobes, or two lobes may be combined into a single lobe. However, it has been observed that the preferred configuration as shown in FIG. 10 has various advantages in providing a good fit to the hoof of an adult horse.

The strap 54 is preferably an elongate and flexible strap having an inner surface 64 made of a loop material of a type configured for releasably engaging a hook material. The opposite outer surface 66 of the strap 54 is preferably made of the same material as the exterior of the bandage 52, such as polyester fiber material. The strap 54 is preferably incorporated onto the bandage 52 by passing the strap 54 though a pair of spaced apart slits 68 and 70 defined through a portion of the bandage 52. The slits 68 and 70 are preferably located adjacent a central portion of the lobe 60f and the strap 54 oriented so that the inner surface 64 of the strap 54 and the long ends of the strap are adjacent the exterior surface 59 of the bandage 52. The length of each end of the strap 54 extending outwardly from the slits 68 and 70 are preferably adjusted to be substantially the same.

The engagement members 56, 57, and 58 are preferably strips of hook material secured to the exterior surface 59 of the bandage 52, as by stitching. The engagement members 56 and 57 are preferably secured adjacent edge portions of the lobe 60f and located outwardly of the slits 68 and 70. The engagement member 58 is preferably located at a central portion of the lobe 60c. As will be appreciated, the strap may alternatively include a surface made of a hook material and the engagement members having loop material.

Turning to FIGS. 11 and 12, the bandage 52 may be applied to the hoof in a manner similar to the bandage 12. For example, the sole of the hoof 40 is placed over the central body portion 62 of the bandage 52 and oriented such that the toe of the hoof 40 is located below the lobe 60c of the bandage 12. If desired, a flexible and elastic wrapping material may be applied to the hoof and ankle portions having medication applied thereto. A preferred wrapping material is a material available under the trademark VET-RAP from the 3M corporation.

Padding, such as the pad 16, is preferably placed under the hoof 40. It will be understood that the pad 16 is suitable for providing comfort attributes and may also serve as a site for receiving medicament and the like. As will be appreciated, the bandage 52 is oriented so that the exterior surface 59 is facing the ground and the opposite adhesive surface faces the hoof.

The lobes 60a and 60e are folded about the hoof 40 and secured to the hoof by the adhesive of the tape material. The lobes 60b and 60d are folded and secured to the hoof 40 and overlie a portion of the lobes 60a and 60e, respectively. The lobe 60c is folded to overly and be secured to the lobes 60b and 60d.

The lobe 60f is then folded up and around the back side of the hoof and the edge portions of the lobe 60f having the engagement members 56 and 57 located to face outward and overlie the lobe 60c, with the adhesive surface thereof securing the lobe 60f in place. As assembled, the strap 54 is located adjacent the back of the hoof with the inner surface 64 of loop material facing the exterior of the bandage 52. The opposite ends of the strap 54 are then tensioned and the inner surface 64 pressed to matingly engage the engagement members 56, 57, and 58 adjacent the toe of the hoof as shown in FIGS. 11 and 12.

FIGS. 13-16

Figure 13:
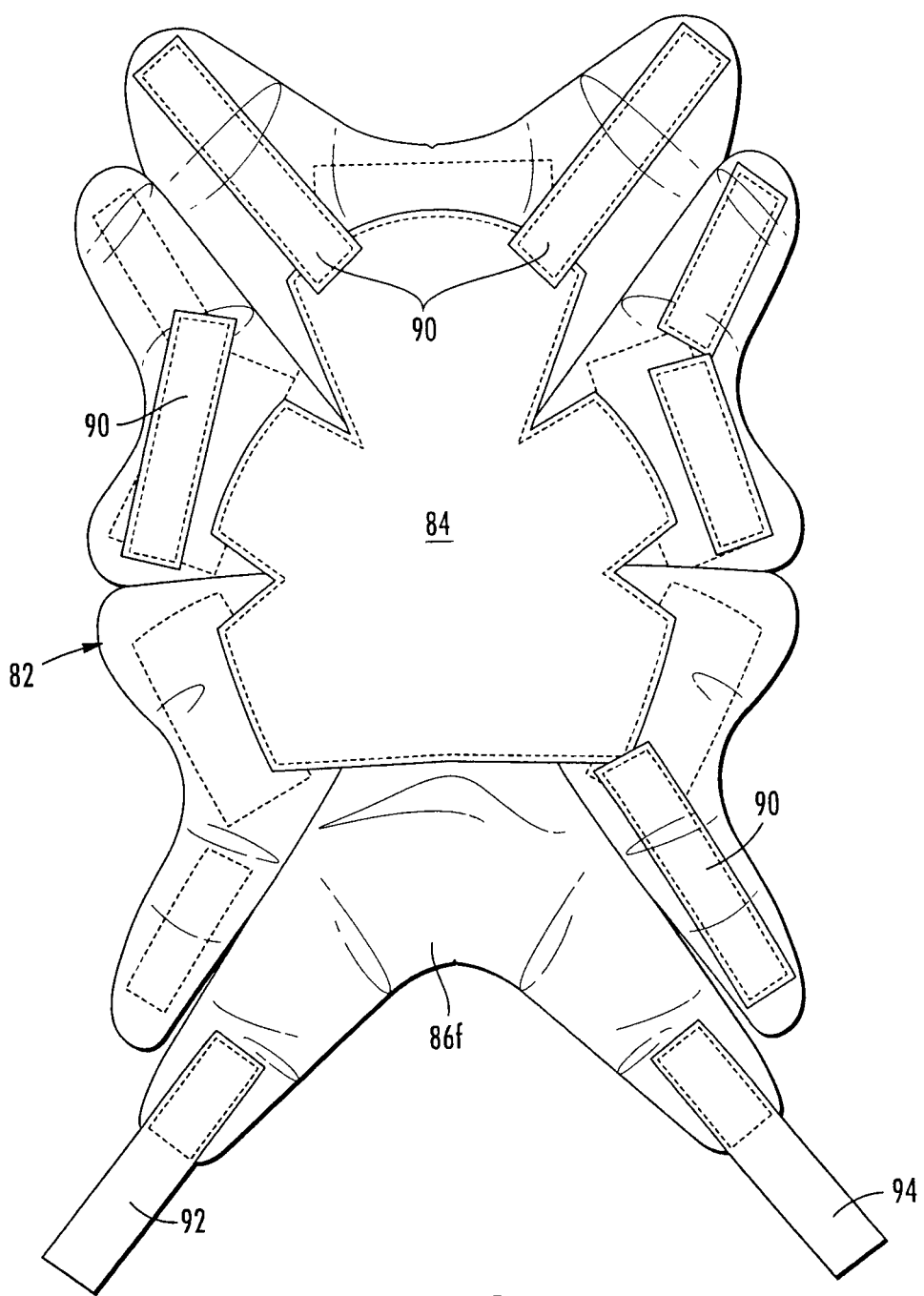
FIGS. 13 and 14 show, respectively, the interior and exterior of yet another embodiment of a bandage as laid flat.
Figure 14:
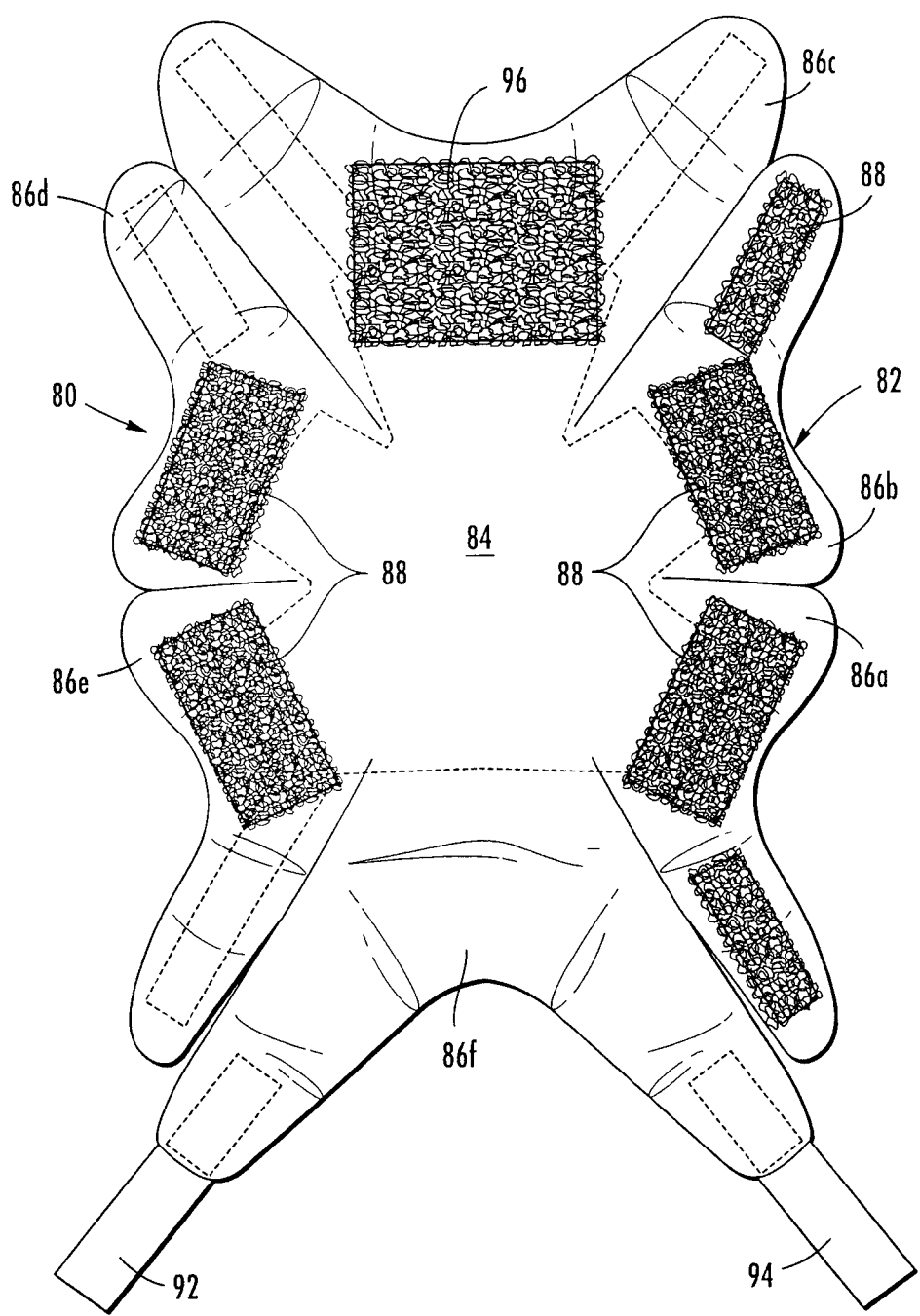
Figure 15:
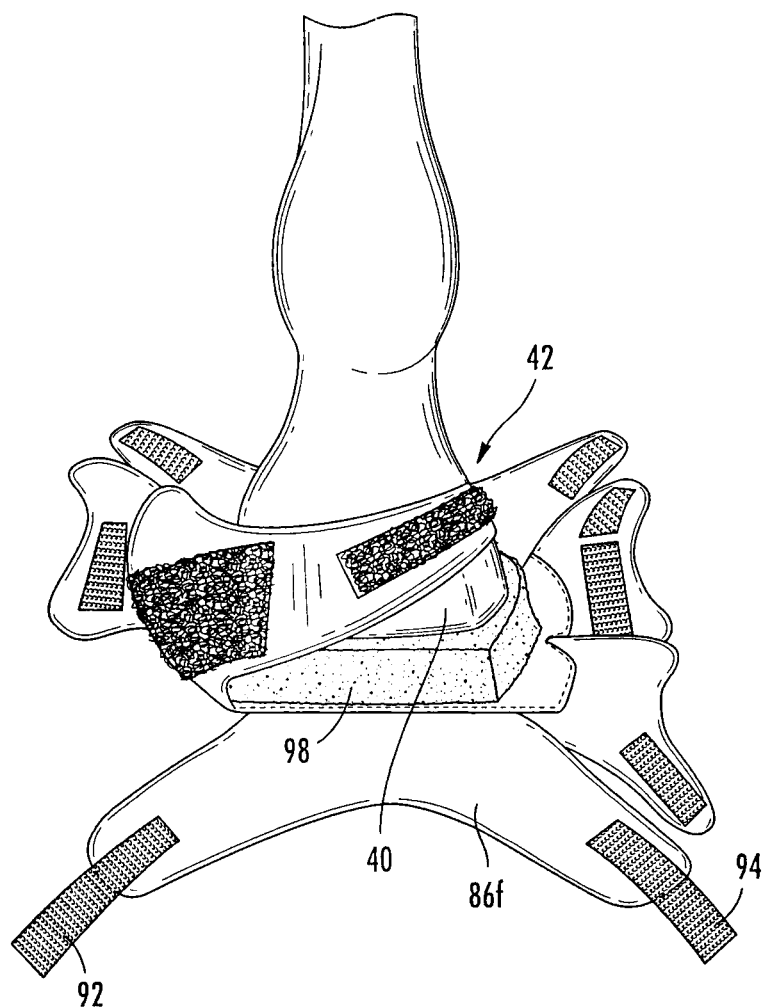
FIGS. 15 and 16 show application of the bandaging system of FIGS. 13 and 14.
Figure 16:
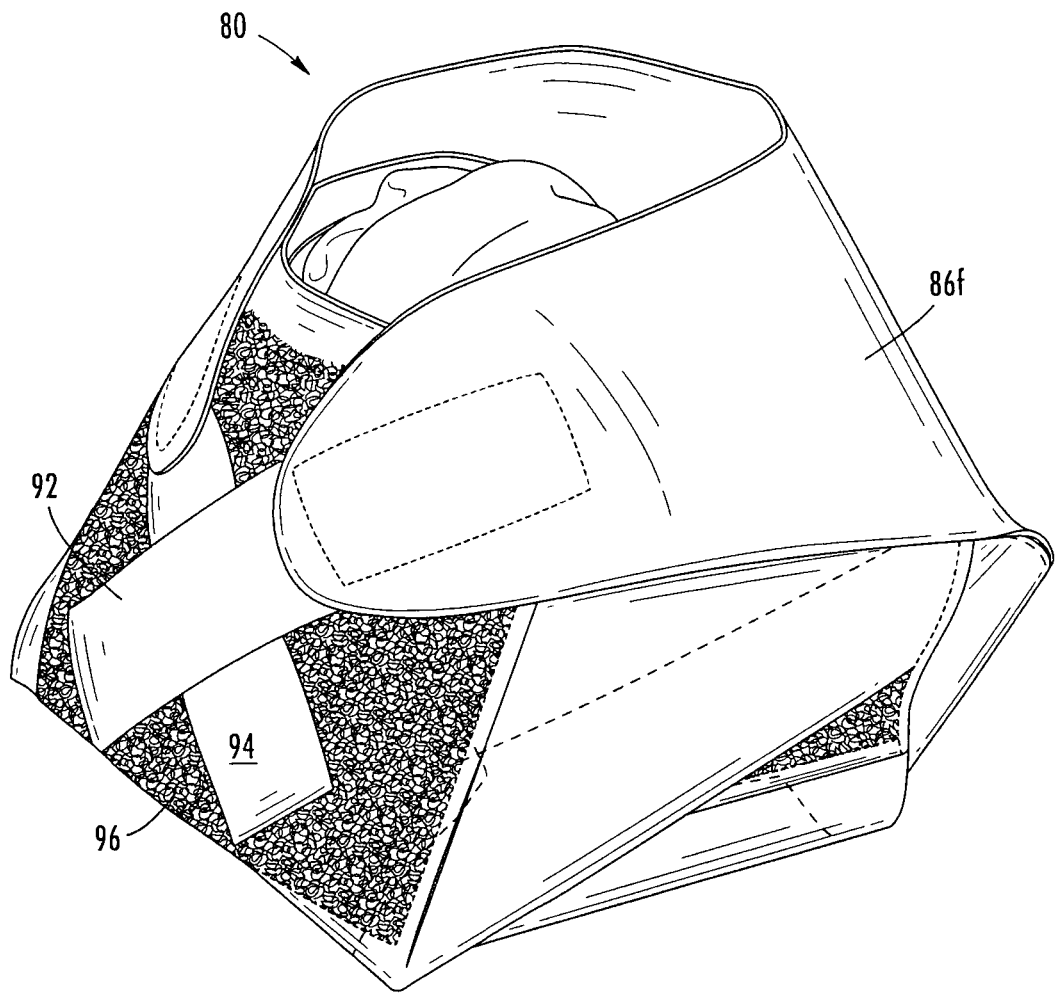

With reference now to FIGS. 13 and 14, there is shown an alternate embodiment of a bandaging system 80. The system 80 is substantially similar to the bandaging system 50, except that instead of having a single strap, such as the strap 54, the ends of a pair of shorter straps extend from opposite sides of the lobe adjacent the back of the hoof. FIGS. 15 and 16 show installation of the system onto a hoof of a horse.

For example, in a preferred embodiment, the system 80 includes a bandage 82 made of a sheet material having a central body portion 84 and a plurality of palmate lobes 86a-86f radiating outwardly from the central body portion. Each of the lobes 86a-86e may include portions of loop or hook material 88 attached to exterior portions thereof, and strips of hook or loop material 90 located on the interior of some of the lobes for mating with the hook or loop material when installing the bandage about the hoof.

The lobe 86f is located to substantially surround a back side of the hoof and includes straps 92 and 94. The straps 92 and 94 are attached to the lobe 86f, as by stitches, and located to extend from opposed sides of the lobe 86f adjacent the back side of the hoof toward a toe of the hoof. The straps 92 and 94 include hook material and are releasably securable to mating hook material 96 attached, as by stitches, to an exterior portion of the bandage 82 adjacent the toe 42 of the hoof 40 when the bandage is installed on the hoof. A pad 98 may be located beneath the hoof.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A bandage for a hoof, comprising: a sheet material having a central body portion and at least six independently foldable palmate lobes radiating outwardly from a central body portion and foldable one over another so as to enable the bandage to lie flat against the profiles of the hoof, one of the lobes located to fold up and substantially surround a back side of the hoof and including straps that extend from opposed sides of such lobe adjacent the back side of the hoof toward a toe of the hoof and which straps are secured to an exterior portion of the bandage adjacent the toe of the hoof when the bandage is installed on the hoof.

2. The bandage of claim 1, wherein the sheet material comprises a tape material.

3. The bandage of claim 1, wherein the straps comprise separate straps extending from opposite sides of the lobe.

* * * * *